United States Patent
Boese et al.

(10) Patent No.: US 7,899,151 B2
(45) Date of Patent: Mar. 1, 2011

(54) OPERATING METHOD FOR A SWIVELING POLYPLANAR IMAGING SYSTEM FOR TIME-RESOLVED IMAGING OF AN OBJECT BEING EXAMINED

(75) Inventors: Jan Boese, Eckental (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 43 days.

(21) Appl. No.: 12/383,422

(22) Filed: Mar. 24, 2009

(65) Prior Publication Data

US 2009/0252287 A1   Oct. 8, 2009

(30) Foreign Application Priority Data

Apr. 2, 2008   (DE) .................. 10 2008 016 891

(51) Int. Cl.
*H05G 1/60* (2006.01)

(52) U.S. Cl. ................... 378/17; 378/4; 378/9

(58) Field of Classification Search ........... 378/4, 378/8, 9, 17, 197
See application file for complete search history.

(56) References Cited

U.S. PATENT DOCUMENTS

| | | | | |
|---|---|---|---|---|
| 5,375,156 A | * | 12/1994 | Kuo-Petravic et al. | 378/9 |
| 2001/0012328 A1 | * | 8/2001 | Koppe et al. | 378/62 |
| 2001/0043671 A1 | * | 11/2001 | Grass et al. | 378/210 |
| 2002/0085681 A1 | * | 7/2002 | Jensen | 378/197 |
| 2002/0181645 A1 | * | 12/2002 | Bruder et al. | 378/8 |
| 2004/0066906 A1 | | 4/2004 | Hornegger et al. | |
| 2004/0208276 A1 | * | 10/2004 | Kaufman | 378/4 |
| 2007/0009080 A1 | * | 1/2007 | Mistretta | 378/4 |

FOREIGN PATENT DOCUMENTS

DE   102 41 184 A1   4/2004

* cited by examiner

*Primary Examiner*—Edward J Glick
*Assistant Examiner*—Alexander H Taningco

(57) ABSTRACT

An operating method for a polyplanar imaging system for time-resolved imaging of an object is provided. First and second data records are recorded at a fan angle $\beta$ from different angular positions by a first and second imaging planes arranged at an offset angle $\gamma$ relative to each other and swiveled through an angle of at least $\phi=180°+\beta$. A third data record is created by selecting projection images from the first data record beginning from a starting angle $\alpha$ and from the second data record so that the third data record covers an angular range of at least $\phi$. Three-dimensional images are reconstructed based on the third data record. The starting angle $\alpha$ is varied for continuously creating the third data record until $\alpha$ has attained its final value. The contrast of projection images in the third data record or of three-dimensional images is evaluated.

18 Claims, 3 Drawing Sheets

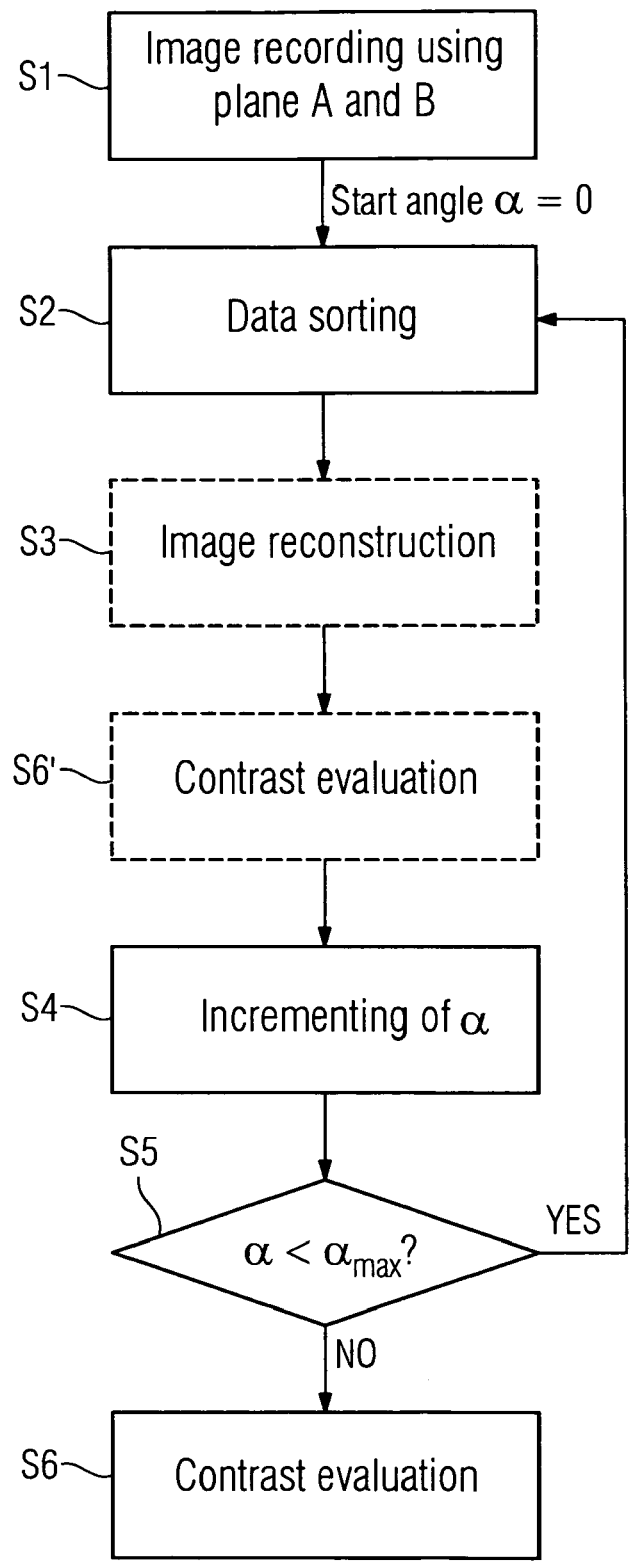

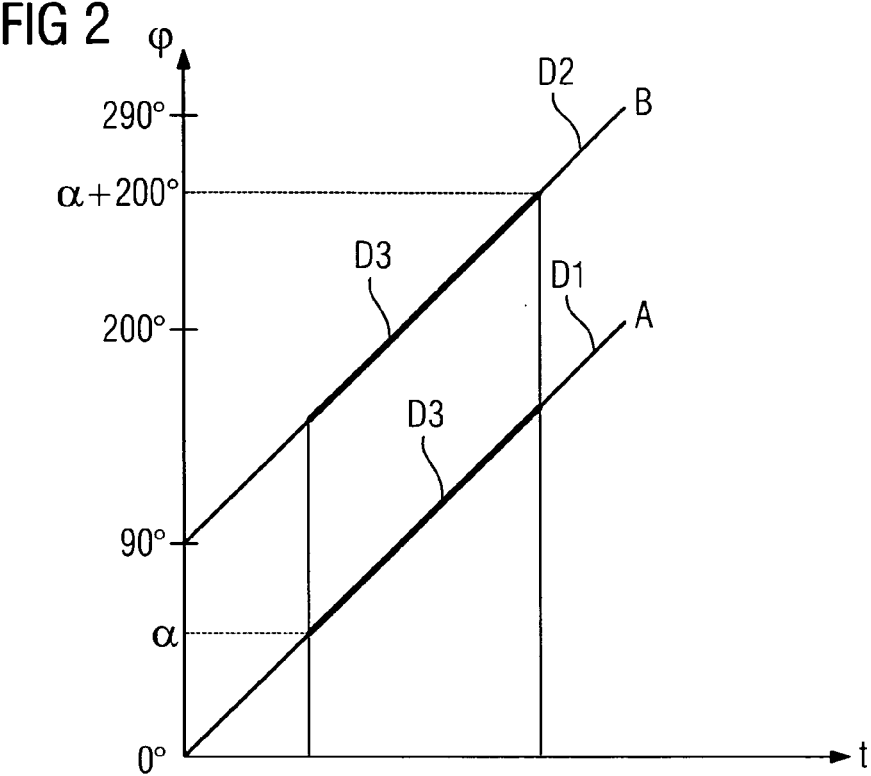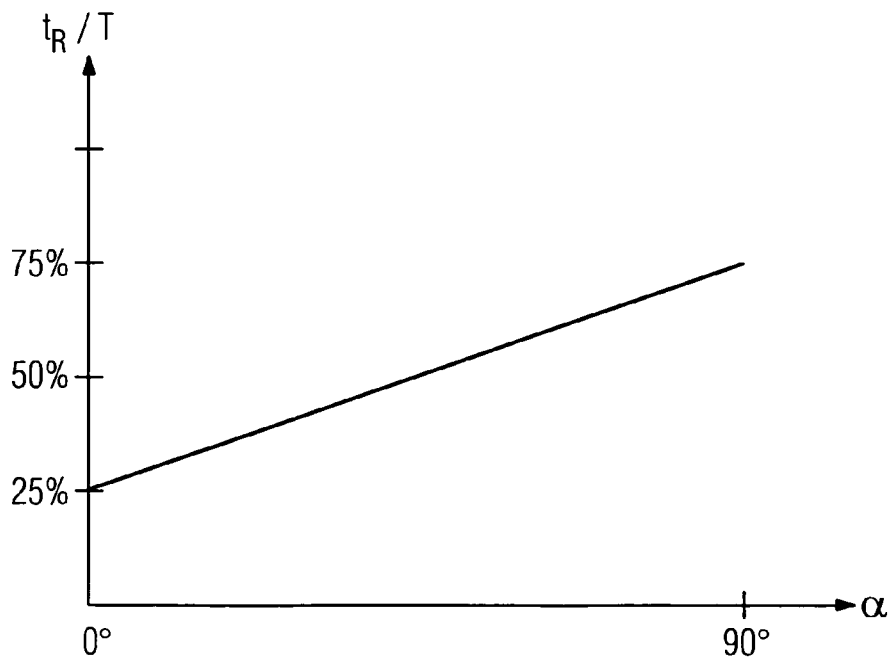

OPERATING METHOD FOR A SWIVELING POLYPLANAR IMAGING SYSTEM FOR TIME-RESOLVED IMAGING OF AN OBJECT BEING EXAMINED

CROSS REFERENCE TO RELATED APPLICATIONS

This application claims priority of German application No. 10 2008 016 891.2 filed Apr. 2, 2008, which is incorporated by reference herein in its entirety.

FIELD OF THE INVENTION

The present invention relates to an operating method for a swiveling polyplanar imaging system for time-resolved imaging of an object being examined, in particular a method for time-resolved cardiac imaging and perfusion imaging by means of an angiography device—as an instance of which a biplanar C-arm device is used herein—and to a corresponding computer program and a data medium on which it is stored, as well as to a swiveling polyplanar imaging system for implementing the operating method. The invention relates further to an imaging system.

BACKGROUND OF THE INVENTION

What is to be understood hereunder by the term "polyplanar imaging system" is an imaging system which for the recording of images has not just one swiveling plane but a plurality thereof, in particular two or three.

The present invention relates particularly to angiography systems as employed for medical interventions performed on the heart, for instance. Angiography systems traditionally produce simple x-ray projection images in which structures such as heart shadows, guide wires, catheters, and catheters filled with a contrast agent are discernible. Angiography devices of modern design typically have a C-shaped arm on one of whose ends an x-ray source and on the other of whose ends an associated x-ray detector is attached. The C-arm can be freely swiveled around a patient-supporting table, thereby allowing two-dimensional realtime x-ray images (fluoroscopic recordings) of the patient to be recorded from many different viewing directions. Rotating the C-arm around the patient will thus also allow angiography systems of such type to produce CT-like 3D images, referred to also as C-arm CT.

In numerous C-arm CT applications a contrast agent has to be injected during recording, lasting typically at least 4 to 5 seconds, in order to emphasize the structures of interest such as vessels or ventricles of the heart. The contrast agent must therein be present as far as possible in a temporally constant concentration during recording. So what matters is very good synchronizing between contrast agent injecting and image recording.

However, it is often not easy to keep the contrast agent for several seconds in precisely the structure intended to be imaged and at the same time prevent other structures from being contrasted. What is particularly problematic are the temporal dynamics associated with representing the left atrium. Said representing is a quite novel and very attractive method for supporting ablation therapies in the case of atrial fibrillation. A preferred protocol or, as the case may be, measuring protocol is concerned with the instant at which the contrast agent is injected into the main pulmonary artery and how quickly measuring takes place. Said agent is transported through the lung, and C-arm CT recording is started precisely when it has traversed the lung and reached the left atrium. The optimal instant for that is, though, different for each patient and not easy to determine.

One possible solution to the problem is to administer a test injection—which is to say a test bolus—prior to actual 3D recording. Quite a small amount of contrast agent is therein injected and the circulation time (which is the time from when the contrast agent is injected until it reaches the structure being examined) is then determined from fluoroscopic images or DSA recordings (DSA=Digital Subtraction Angiography).

However, that method poses various problems: Firstly, a substantial amount of contrast agent is used for it, typically 20 ml with 80 ml for 3D recording. Secondly, owing to the smaller amount of contrast agent the test bolus does not have the same dynamic properties as the subsequent, actual measuring bolus. Thirdly, the timing is often only poorly discernible from DSA recordings because they are projection recordings that do not adequately resolve the three-dimensional anatomy. Fourthly, there can be a difference between the test bolus and final recording owing to changes in circulation time (due to pulse and blood pressure variations).

In the prior art a biplanar C-arm x-ray system's second plane offers the advantage of being able to halve the recording time by having the two planes rotate simultaneously, with each only covering an angular range of approximately 100°. The problem with synchronizing then becomes even more critical, however, because the time for a rotation run is shorter. The term "rotation run" therein means that a C-arm is swiveled across an angular range of (at least) 180°+fan angle, with as a rule 50 to 500 images being recorded. The "fan angle" corresponds to the angle at which the x-ray source emits its x-rays and is as a rule approximately 20°.

Summarizing, it can be stated that the test-bolus method provides at best a very inadequate solution to the problem.

SUMMARY OF THE INVENTION

The object of the present invention is hence to provide an operating method for a swiveling polyplanar imaging system for time-resolved imaging of an object being examined along with a corresponding computer program—possibly stored on a data medium—by means of which the disadvantages known from the prior art will have been eliminated and improved measuring results, in particular representations of the heart and vessels, will be possible. The aim in particular is, without using a bolus, to make vascular representations possible by means of which images can be obtained that exhibit a maximum possible contrast resolution in terms of the cardiological structures requiring to be imaged. The aim is furthermore to provide a swiveling polyplanar imaging system for implementing the operating method.

The object is achieved by the independent claims.

Advantageous developments of the invention are the subject of the dependent claims.

The inventive method offers the advantage that after a 3D rotational recording has been made a series of images can be produced that correspond to different instants. Thus the image that tallies best with a contrast agent injection can be selected after a recording has been made. It will hence no longer be necessary after the contrast agent has been administered to estimate the optimum instant to start recording as precisely as hitherto.

It will consequently in most cases be possible to dispense with recording a test bolus exhibiting the aforementioned disadvantages.

The method can generally speaking be applied in all cases in which retrospective synchronizing—meaning subsequent matching—of a C-arm CT recording with another process (contrast agent injecting, moving) that can change over time is desired or even necessary. For the cardiovascular representation, that means that the initial measurement, utilizing both measuring planes, across a significantly greater angle than that absolutely necessary of 180°+fan angle provides a kind of time buffer which on the one hand can be used for improving image quality through retrospectively selecting a changed recording instant and, on the other, will enable image recording or, as the case may be, the instant at which it takes place to be subsequently matched to contrast agent injecting.

According to a preferred embodiment variant of the inventive method the offset angle between the two imaging planes is 80° to 100°, in particular 90°, the initial value of the starting angle is 0°, and the final value of the starting angle is a maximum and equal to said offset angle.

It is preferred for the starting angle to be incremented in steps of 0.1° to 2.0°, preferably 0.2° to 1.5°. The starting angle can of course also be decremented beginning from its maximum.

It is furthermore preferred for the third data record to be created in such a way at the second step by selecting projection images that an angular range of at least $\alpha$ to $\alpha+(180°+\beta)/2$ will be covered from the first data record beginning from the starting angle $\alpha$ and an angular range of at least $\alpha+(180°+\beta)/2$ to $\alpha+(180°+\beta)$ will be covered from the second data record. An optimal result can be achieved thereby.

It can alternatively be advantageous in certain cases to create the third data record at the second step by selecting projection images specifically in such a way that an angular range of at least $\alpha$ to $\alpha+\theta+\beta$ will be selected from the first data record beginning from the starting angle $\alpha$ and an angular range of at least $\alpha+\theta+\beta$ to $\alpha+180°+\beta$ will be selected from the second data record, with its preferably generally applying to $\theta$ that $60°\leq\theta\leq120°$. $\theta$ is furthermore preferably between 70° and 110°, in particular between 80° and 100°, and particularly preferably between 85° and 95°.

It has proved favorable to perform contrast evaluating at the sixth step by maximizing the overall grayscale value of the images used for evaluating with varying of the starting angle.

Particularly accurate and comprehensive evaluating can be achieved if all the grayscale values of all the pixels of all the projection images in the third data record are summated.

Less compute-intensive evaluating can conversely be performed if all the grayscale values of all the pixels of the first and last projection image from among the projection images in the third data record are summated.

An alternative approach thereto is to summate all the grayscale values of all the pixels within a randomly sampled quantity—for example every fifth or tenth image—of projection images in the third data record.

The range of relevance to evaluating can be selectively influenced by summating all the grayscale values of the pixels of the projection images in the third data record that are located within a range defined by a user or determined automatically.

The evaluating potential can be extended if prior to evaluation of the third data record's projection images already obtained by means of the inventive method a corresponding set of projection images is produced with the administering of a contrast agent having been changed (or not having taken place) and is subtracted from the existing third projection images in order to produce DSA images.

As the imaging system, a biplanar C-arm angiography system is preferably employed as a medical x-ray system.

The administering of contrast agent can be standardized and, by means of an injector, automated by synchronizing the injecting of a contrast agent with the start of the first step. The contrast agent will therein typically be injected such as to produce complete, homogeneous contrasting during the first step.

A particular advantage of the invention is that the temporal dynamics of contrast agent injecting can be calculated by means of the evaluation and that the tissue perfusion and/or dynamic vascular representation can be calculated from the temporal dynamics of contrast agent injecting.

The inventive swiveling polyplanar imaging system for time-resolved imaging of an object being examined includes a first and second imaging plane that are arranged at an offset angle $\gamma$ relative to each other and record at a fan angle $\beta$. Provided in each imaging plane are a source and detector arranged mutually opposite in terms of their swiveling axis and of the object being examined and serving to record first and second projection images from different angular positions. The projection images are therein recorded with the imaging planes being swiveled through in each case an angle of at least $\phi=180°+\beta$ for producing a first data record recorded by the first imaging plane and a second data record recorded by the second imaging plane. The polyplanar imaging system furthermore has a control and evaluation system for controlling it. The control and evaluation system is embodied for, on the one hand, driving the source and detector in a manner suitable for image recording and, on the other, for evaluating the recorded data records in accordance with one of the above-described methods.

BRIEF DESCRIPTION OF THE DRAWINGS

The invention is explained in more detail below with the aid of a preferred exemplary embodiment and with reference to the schematic figures, in which:

FIG. 1 is a flowchart showing the basic flow of an inventive operating method for time-resolved cardiac imaging and perfusion imaging, FIG. 2 shows the correlation between the angles and data records arising while the inventive method is being implemented, FIG. 3 shows the displacement in recording time caused by varying the starting angle.

DETAILED DESCRIPTION OF THE INVENTION

Figure 4:
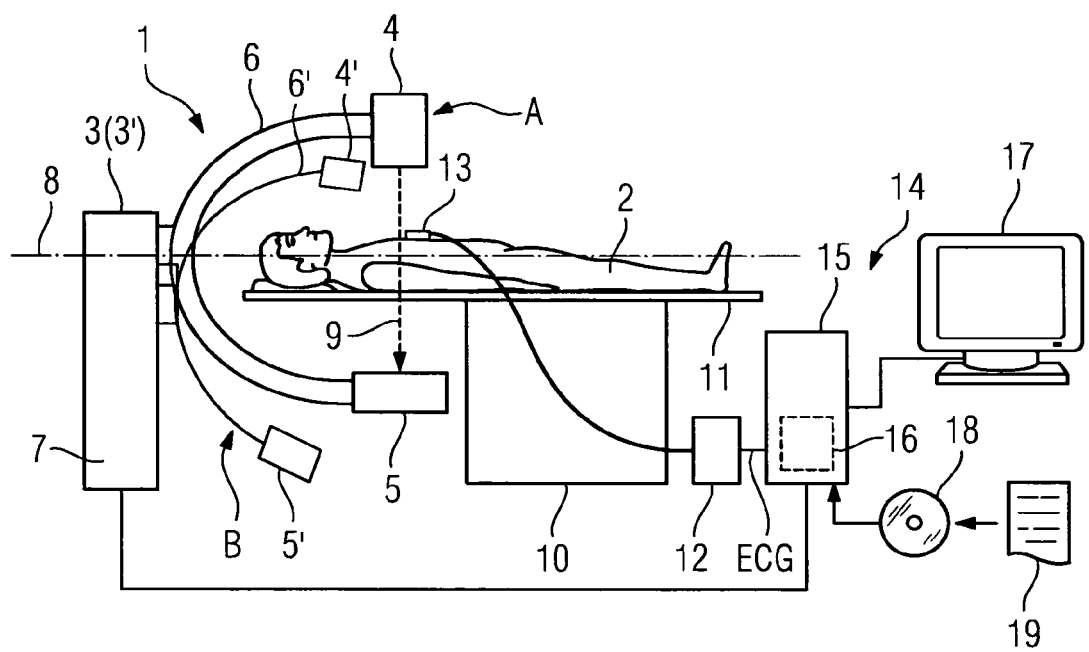
FIG. 4 shows an inventively embodied biplanar C-arm system on which the inventive operating method can be implemented.

In its preferred embodiment variant the invention does not use a typically employed monoplanar x-ray system for image recording but, instead, a biplanar C-arm x-ray system.

FIG. 4 is a schematic of a device 1 for producing a three-dimensional image data record of an object. The device 1 is a biplanar x-ray tomograph, in particular a biplanar 3D rotational angiography system. The object being examined is the chest region, in particular the heart, of a patient 2.

The device 1 includes in a first imaging plane A a recording unit 3 having an x-ray tube 4 and an x-ray detector 5. The x-ray tube 4 and x-ray detector 5 are attached mutually opposite on the ends of what is termed a C-arm 6 and, along with the latter, define the first imaging plane A. The C-arm 6 is in turn mounted, capable of rotating around an isocentric axis 8, approximately centrally on a stand 7. By swiveling the C-arm 6 with respect to the stand 7 the x-ray tube 4 and x-ray detector 5 can therein be turned such that a central beam 9 of the x-rays emitted by the x-ray tube 4 toward the x-ray detector 5 can within a recording plane perpendicular to the isocentric axis 8 be swiveled with respect to the surrounding space into any projection angle of at least 180° plus what is termed the fan angle, with the central beam 9 being at all times oriented on the isocentric axis 8.

The device 1 also includes in a second imaging plane B (only intimated perspectively) a recording unit 3' having an x-ray tube 4' and an x-ray detector 5'. The x-ray tube 4' and x-ray detector 5' are attached mutually opposite on the ends of a second C-arm 6' and, along with the latter, define the second imaging plane B arranged displaced by an offset angle γ of ideally 90° relative to the first imaging plane A.

The device 1 further includes a patient-supporting table 10 having a table plate 11 on which the patient 2 is positioned while being examined such that the longitudinal axis of his/her body is approximately aligned with the isocentric axis 8 of the recording unit 3. The table plate 11 can for the examination being performed be slid into the opening of the C-arm 6 such that the region being examined of the body of the patient 2 will come to lie between the x-ray tube 4 and x-ray detector 5.

The device 1 further includes an ECG unit 12 having a number of ECG sensors 13 that can be attached in a known manner to the body of the patient 2 for recording an electrocardiogram (ECG), meaning an electric signal reproducing the cardiac activity of the patient 2.

The device 1 further includes a control and evaluation system 14. The control and evaluation system 14 includes a data processing system 15 in which are implemented, besides operating and control functions (not shown in further detail), a read device for a computer program 19 stored on a data medium 18 such as, for example, a CD or a USB stick as well as an evaluation unit 16 for producing a three-dimensional (3D) image data record of the region being examined of the body of the patient 2. The control and evaluation system 14 further includes input/output means 17 such as, for instance, a display screen and a keyboard and mouse, and suchlike, for entering control instructions and displaying status variables, examination results, etc.

Digital image data is fed to the evaluation unit 16 by the recording unit 3 in the course of the method implemented by the device 1. An ECG signal ECG of the patient 2 is also fed to the evaluation unit 16 by the ECG unit 12.

According to FIG. 1 the inventive method for time-resolved 3D image generation comprises various steps.

a) Image Recording

For a 3D reconstruction it is necessary for a C-arm to execute a rotation run through an angular range of (at least) 180°+fan angle β and for as a rule 50 to 500 images to be recorded while that is taking place. The simplified assumption below is that the fan angle β is 20° and hence an angular range of 200° has to be covered. Said fan angle β can also have different values, for example in the 0° to 40° range, though in particular in the 10° to 30° range. The two C-arms of the planes A and B respectively are arranged mutually displaced at an offset angle γ, with γ here being assumed to be 90° with no restrictions placed on general applicability. So the two C-arms start at initial positions offset by 90° (see FIG. 2). The two C-arms rotate at step S1 through an angular range of 200° once recording has started, meaning that the first C-arm A records a first data record D1 in the 0° to 200° range and the second C-arm B records a second data record D2 in the 90° to 290° range.

b) Data Sorting

A new data record D3 is then inventively compiled at step S2 from the recorded data records D1 and D2 of the two planes A and B respectively: Beginning from a starting angle α, an angular range of α to α+100° from plane A is combined with a range of 100°+α to 200°+α from plane B to produce a new data record D3 covering 200°.

The starting angle α can therein in that embodiment variant vary between 0° and 90°. The start is as a rule a starting angle α=0°. The relevant angular ranges are shown by way of example in FIG. 2. The thin lines on the straight lines designated A and B therein represent the two recorded data records D1 and D2 respectively and the thick lines represent the data record D3 (for the reconstruction selected in this example). The data record D3 ends on the straight line A at the angle (in this case approximately 140°, corresponding to α=50°) at which it starts on the straight line B. When the two partial data records D1 and D2 are combined, possible gaps in the transitional region due to inconsistencies can if necessary be obviated by a soft transient weighting.

c) Image Reconstructing

The thus compiled new data record D3 is fed to the rest of the image reconstruction (filtered back projection on the Feldkamp principle, for example).

Finally, α will in accordance with step S4 continue being incremented and steps S1 to S4 will in accordance with step S5 continue being repeated until α has attained its maximum $α_{max}$ (in this case 90°, corresponding to γ).

d) Evaluating

The manner in which the object underlying the invention is achieved is that the series of projection images and/or three-dimensional images exhibiting maximum contrast resolution in terms of the cardiological structures requiring to be imaged (the left atrium, for example) is reconstructed by varying α. The contrast of the third projection images used for evaluating is for that purpose finally determined in accordance with step S6. As shown with a dashed line in FIG. 1, it is possible for a corresponding step S6', similar to step S6, to be performed sooner, specifically before α is incremented. It is alternatively also possible for a corresponding evaluation step to be performed in parallel with another step if that is expedient.

For contrast evaluating at step S6, the parameter or, as the case may be, starting angle α can for that purpose be determined automatically for example by means of the following procedures:

1—Evaluating all the projection images in the series by summating all the grayscale values of all the pixels and maximizing the overall grayscale value, with varying of α.

2—Evaluating the first and last projection image in the series by maximizing the overall grayscale value, with varying of α.

3—Evaluating a randomly sampled quantity of projection images (for example every tenth image) and maximizing the grayscale value, with varying of α.

4—Same as one of steps 1 to 3, though with evaluating being performed not across all pixels in the projection images but only across an ROI (region of interest, for example a user-selected spherical sector in the C-arm system's isocenter) that is determined automatically (for example through image recognition applied to organ structures) or defined by the user.

5—Steps 1 to 4 can optionally also be applied to DSA images. That means that the determining of α is applied to subtracted images. A 3D x-ray rotational recording without the injecting of a contrast agent is for that purpose produced in addition to the projection images enriched with contrast agent (projection image recording and 3D data reconstructing are performed as described above, meaning using two synchronously rotating C-arm planes). One of procedures 1 to 4 is then applied to the subtracted data ("images with contrast agent" minus "images with no contrast agent").

With the above procedures 1, 4, and 5 it is moreover possible in addition to or instead of evaluating the pixels to evaluate the voxels in the three-dimensional images produced therefrom, with a better contrast resolution as a rule being achievable through evaluating three-dimensional images than in the case of evaluating two-dimensional projection images.

The entire method described above that is to be implemented on a biplanar system can also be analogously extended to include angiography systems having three or more planes.

Setting or, as the case may be, successively incrementing the parameter $\alpha$ between 0° and 90° causes the mean value $t_R$ of the recording time T to be displaced between 25% T and 75% T. That correlation is shown in FIG. 3. The recording time T is therein defined as the time between when the C-arms start rotating and the instant at which an individual image is actually recorded. A series of images can in that way be produced subsequently with different reconstruction times.

It was assumed in the foregoing that $\alpha_{max}=\gamma$. A correspondingly larger value can, however, be selected for $\alpha_{max}$ if the C-arms traverse a larger angle than the absolutely necessary 180° (plus fan angle).

It is emphasized that the invention's features described with reference to the specific embodiment variant presented, such as, for instance, the precise sequence of individual steps and their flow, the dimensioning of the different angles, and the type of images used for evaluating, can also be exhibited by other embodiment variants unless indicated otherwise or automatically precluded for technical reasons.

The invention claimed is:

1. An operating method for a swiveling polyplanar imaging system for time-resolved imaging of an object, the swiveling polyplanar imaging system comprising a first and a second imaging planes arranged at an offset angle $\gamma$ relative to each other and record at a fan angle $\beta$, the method comprising:
    recording a first set of projection images of the object by the first imaging plane from a first set of different angular positions, the first imaging plane being swiveled through at least an angle of $\phi=180°+\beta$;
    generating a first data record from the first set of projection images;
    recording a second set of projection images of the object by the second imaging plane from a second set of different angular positions, the second imaging plane being swiveled through at least the angle of $\phi=180°+\beta$;
    generating a second data record from the second set of projection images;
    storing the first data record and the second data record;
    creating a third data record by selecting the projection images from the first data record beginning from a starting angle $\alpha$ and the projection images from the second data record so that projection images in the third data record covers at least the angular range of $\phi$;
    varying the starting angle $\alpha$ from an initial value to a final value $\alpha_{max}$;
    continuously repeating the creating of the third data record and the varying of the starting angle $\alpha$ until the starting angle $\alpha$ has attained the final value $\alpha_{max}$; and
    evaluating a contrast of the projection images in the third data record,
    wherein three-dimensional images are reconstructed based on the third data record and a contrast of the three-dimensional images is evaluated, and
    wherein the contrast of the projection images in the third data record and the contrast of the three-dimensional images are evaluated by maximizing an overall grayscale value of the projection images in the third data record and an overall grayscale value of the three-dimensional image.

2. The method as claimed in claim 1, wherein the offset angle $\gamma$ is between 80° to 100°.

3. The method as claimed in claim 1, wherein the initial value of the starting angle $\alpha$ is 0° and the final value $\alpha_{max}$ of the starting angle $\alpha$ equals to the offset angle $\gamma$.

4. The method as claimed in claim 1, wherein the starting angle $\alpha$ is varied in a step of 0.1° to 2.0° range.

5. The method as claimed in claim 1, wherein the third data record is created by selecting the projection images from the first data record that cover an angular range from the starting angle $\alpha$ to $\alpha+(180°+\beta)/2$ and the projection images from the second data record that cover an angular range from $\alpha+(180°+\beta)/2$ to $\alpha+(180°+\beta)$.

6. The method as claimed in claim 1, wherein the third data record is created by selecting the projection images from the first data record that cover an angular range from the starting angle $\alpha$ to $\alpha+\theta+\beta$ and the projection images from the second data record that cover an angular range of $\alpha+\theta+\beta$ to $\alpha+180°+\beta$ with the $\theta$ in a range of $30°\leq\theta\leq150°$.

7. The method as claimed in claim 1, wherein the evaluation is performed with the varying of the starting angle $\alpha$.

8. The method as claimed in claim 1,
    wherein the overall grayscale value of the projection images in the third data record is a summation of grayscale values of pixels of the projection images in the third data record, and
    wherein the overall grayscale value of the three-dimensional images is a summation of grayscale values of voxels of the three-dimensional images.

9. The method as claimed in claim 8, wherein the grayscale values of the pixels of the projection images in the third data record and the voxels of the three-dimensional images are located within a range defined by a user or determined automatically.

10. The method as claimed in claim 1, wherein the overall grayscale value of the projection images in the third data record is a summation of grayscale values of pixels of each first and last projection images among the projection images in the third data record.

11. The method as claimed in claim 1, wherein the overall grayscale value of the projection images in the third data record is a summation of grayscale values of pixels of randomly sampled quantity of the projection images in the third data record.

12. The method as claimed in claim 1, wherein an additional first set and an additional second set of projection images are recorded with an administering of a contrast agent and are subtracted from the corresponding first set and the second set of the projection images to generate digital subtraction angiography images that are evaluated.

13. The method as claimed in claim 1, wherein the imaging system is an x-ray system.

14. The method as claimed in claim 1, wherein a contrast agent is injected synchronized with start of the recording.

15. The method as claimed in claim 14, wherein a temporal dynamics of the contrast agent is calculated by the evaluation.

16. The method as claimed in claim 15, wherein a tissue perfusion or a dynamic vascular representation is calculated from the temporal dynamics of the contrast agent.

17. A non-transitory computer readable medium having a computer program executable for a control and evaluation system of a swiveling polyplanar imaging system for time-resolved imaging of an object, the swiveling polyplanar imaging system comprising a first and a second imaging planes arranged at an offset angle $\gamma$ relative to each other and record at a fan angle $\beta$, the computer program comprising:

a computer subroutine that:
generates a first data record from a first set of project images of the object recorded by the first imaging plane from a first set of different angular positions, the first imaging plane being swiveled through at least an angle of $\phi=180°+\beta$;
generates a second data record from a second set of project images of the object recorded by the second imaging plane from a second set of different angular positions, the second imaging plane being swiveled through at least the angle of $\phi=180°+\beta$;
creates a third data record by selecting projection images from the first data record and project images from the second data record beginning from a starting angle $\alpha$ so that projection images in the third data record covers at least the angular range of $\phi$;
continuously repeats the creating of the third data record by varying the starting angle $\alpha$ until the starting angle $\alpha$ has attained a final value $\alpha_{max}$; and
evaluates a contrast of the projection images in the third data record,
wherein three-dimensional images are reconstructed based on the third data record and a contrast of the three-dimensional images is evaluated, and
wherein the contrast of the projection images in the third data record and the contrast of the three-dimensional images are evaluated by maximizing an overall grayscale value of the projection images in the third data record and an overall grayscale value of the three-dimensional image.

18. A swiveling polyplanar imaging system for time-resolved imaging of an object, comprising:

a first imaging plane that records at a fan angle $\beta$ a first set of projection images of the object from a first set of different angular positions, the first imaging plane being swiveled through at least an angle of $\phi=180°+\beta$;
a second imaging plane arranged at an offset angle $\gamma$ relative with the first imaging plane that records at the fan angle $\beta$ a second set of projection images of the object from a second set of different angular positions, the second imaging plane being swiveled through at least the angle of $\phi=180°+\beta$; and
a control and evaluation system that:
generates a first data record from the first set of the projection images,
generates a second data record from the second set of the projection images,
creates a third data record by selecting the projection images from the first data record and the projection images from the second data record beginning from a starting angle $\alpha$ so that projection images in the third data record covers the angular range of $\phi$,
continuously repeats the creating of the third data record by varying the starting angle $\alpha$ until the starting angle $\alpha$ has attained a final value $\alpha_{max}$, and
evaluates a contrast of the projection images in the third data record,
wherein three-dimensional images are reconstructed based on the third data record and a contrast of the three-dimensional images is evaluated, and
wherein the contrast of the projection images in the third data record and the contrast of the three-dimensional images are evaluated by maximizing an overall grayscale value of the projection images in the third data record and an overall grayscale value of the three-dimensional image.

* * * * *